US011851148B2

(12) United States Patent
Holopainen et al.

(10) Patent No.: US 11,851,148 B2
(45) Date of Patent: Dec. 26, 2023

(54) ANTIFOG SCUBA MASK

(71) Applicants: Reima K. Holopainen, Zufikon (CH); Thomas Burger, Beinwil am See (CH)

(72) Inventors: Reima K. Holopainen, Zufikon (CH); Thomas Burger, Beinwil am See (CH)

(73) Assignee: Johnson Outdoors Inc., Racine, WI (US)

( * ) Notice: Subject to any disclaimer, the term of this patent is extended or adjusted under 35 U.S.C. 154(b) by 87 days.

(21) Appl. No.: 17/674,617

(22) Filed: Feb. 17, 2022

(65) Prior Publication Data
US 2022/0306253 A1    Sep. 29, 2022

Related U.S. Application Data

(60) Provisional application No. 63/165,612, filed on Mar. 24, 2021.

(51) Int. Cl.
B63C 11/12    (2006.01)
A61F 9/02    (2006.01)

(52) U.S. Cl.
CPC .............. B63C 11/12 (2013.01); A61F 9/029 (2013.01)

(58) Field of Classification Search
CPC ...................................................... B63C 11/12
See application file for complete search history.

(56) References Cited

U.S. PATENT DOCUMENTS

| 2,612,639 | A | * | 10/1952 | Christensen | ............ A61F 9/028 165/111 |
| 6,470,696 | B1 | * | 10/2002 | Palfy | ...................... G01N 25/56 62/3.4 |
| 6,886,351 | B2 | | 5/2005 | Palfy et al. | |
| 7,410,254 | B2 | | 8/2008 | Goodis | |
| 8,445,817 | B2 | | 5/2013 | Duchayne et al. | |
| 8,566,962 | B2 | | 10/2013 | Cornelius | |
| 9,210,737 | B2 | | 12/2015 | Cornelius | |
| 10,398,601 | B2 | | 9/2019 | Cornelius et al. | |
| 2009/0025125 | A1 | | 1/2009 | Jou | |
| 2013/0043233 | A1 | | 2/2013 | Elser et al. | |
| 2016/0000600 | A1 | * | 1/2016 | Lee | ........... A61F 7/00 607/109 |
| 2018/0000648 | A1 | | 1/2018 | McCulloch et al. | |
| 2018/0325736 | A1 | | 11/2018 | O'Malley et al. | |

FOREIGN PATENT DOCUMENTS

WO    WO 2020/016839 A1    1/2020

* cited by examiner

Primary Examiner — F Griffin Hall
(74) Attorney, Agent, or Firm — Reinhart Boerner Van Deuren P.C.

(57) ABSTRACT

An underwater mask including a condensing member is provided. The mask includes a lens exposed to ambient water as well as to an air compartment of the mask that is adjacent a diver's face. The mask includes a condensing member that has an inner surface that is exposed to the air compartment and that is configured to promote condensing of moisture within the air within the air compartment thereon prior to the moisture condensing on an inner surface of the lens. The condensing member may be passive and rely on thermal conductivity properties of the member or be actively electrically controlled.

13 Claims, 2 Drawing Sheets

ANTIFOG SCUBA MASK

CROSS-REFERENCE TO RELATED PATENT APPLICATIONS

This patent application claims the benefit of U.S. Provisional Patent Application No. 63/165,612, filed Mar. 24, 2021, the entire teachings and disclosure of which are incorporated herein by reference thereto.

FIELD OF THE INVENTION

This invention generally relates to underwater masks.

BACKGROUND OF THE INVENTION

Divers wear a sealed mask underwater because human eyes can focus properly only when the cornea is facing air. An underwater mask consists includes the main elements of a lens, typically of tempered glass, in the front, a sealing skirt at the sides, a frame holding the skirt on the glass, and a strap extending around the wearer's head holding the underwater mask on the face of the wearer. In some mask designs, the frame is eliminated by attaching the skirt directly to the glass.

An air compartment is formed by the lens and the flexible sealing skirt. The sealing skirt closes the air space towards the diver's face and the flexibility allows small pressure changes. However, when the diver goes deeper, the air in the mask compresses as the ambient pressure is increased (decent of 10 m of salt water corresponds to 1 bar).

Therefore, the diver's nose must be in communication with the air compartment so that the air compartment can be equalized. Even if the underwater mask is perfectly sealed from the surrounding water, the equalizing air from the diver's nose has 100% relative humidity at airway temperature, which is higher than the surrounding water temperature.

Also, the diver's skin covered by the mask has a higher temperature than the surrounding water. As such, the air compartment of the mask has a higher temperature than the surrounding water. Because the air compartment is closed and the relative humidity at immersion is nearly 100%, the tau point (condensation) is first reached at the coldest surface inside of the mask.

Typically, the lens has a thermal conductivity of approximately 0.8 W/m K and silicon rubber commonly used for the skirt has a thermal conductivity of 0.2 W/m K. Due to the higher thermal conductivity of the lens, the inner surface of the lens will be colder than the inner surface of the rest of the mask. As such, the moisture in the air within the air compartment will condense on the inner surface of lens and form fog and other condensate droplets, which disturbs or otherwise inhibits the diver's vision.

To remove the fog, divers need to flood the mask and clear it by exhaling through the nose. When water is removed from the air compartment, the surface pressure of the water at the inner side of the glass forms a film that wipes the glass clean of the fog forming droplets. At the same time, the temperature of the air compartment is dropped close to ambient water temperature. However, the temperature increases again due to higher surface temperature of the skin and higher temperature from the nose exhaled air. Thus, the condensation and fogging process repeats.

Attempts to avoid the condensation and fogging have been made. For example, the lens surface(s) can be treated before being submerged in the water with chemicals or using saliva, which reduce the water surface tension and cause the droplets to form a transparent film instead of individual clear vision disturbing pearls. Over time, the chemicals and saliva are diluted by the water and the effect is, therefore, not permanent.

In car windshields, the fogging can be prevented by heating and blowing a warm dry air with the ventilation fan to the glass inner side. In skiing and outdoors goggles a double isolating lens in the front and proper ventilation with the ambient air removes the fog. Further, the effect can be forced by heating the glass with electricity.

A diving mask could be flushed with the dry air from the diver's air supply tank. However, this would need a physical hose connection to the diver's regulator and this method is practical only when using a diving helmet or a full face mask.

In underwater cameras, the fogging issue is prevented by including silica gel packs inside the camera, which reduce the relative humidity within the camera. However, underwater cameras are completely sealed when operated underwater and underwater masks get more moist air during the dive, such as when the diver equalizes the pressure inside of the mask.

Heating the lens of the underwater mask requires a lot of electrical power because the ambient water at the outer surface has a thermal conductivity of 0.6 W/m K in comparison to air which has a thermal conductivity of 0.024 W/m K. Thus, heating energy flows mainly to surrounding water.

Therefore, there exists a need in the art for improved underwater masks and methods of preventing fogging of the lens of an underwater mask.

BRIEF SUMMARY OF THE INVENTION

Examples of the disclosure provide new and improved underwater masks and in particular underwater masks that inhibit fogging or condensation of the lens(es) thereof. Methods related to the underwater masks are also provided.

In an example, an underwater mask includes first lens, a skirt and a condensing member. The skirt contacts a wearer and supports the first lens. The first lens and skirt form an air compartment that will be forward of the wearer's face in use. The first lens has an inner side facing the air compartment and an outer side opposite the inner side facing away from the air compartment. The outer side would generally be exposed to the ambient water in use. The condensing member is operably carried by the skirt and is in operable thermal communication with the air compartment. The condensing member is configured to condense moisture within the air of the air compartment prior to the moisture within the air of the air compartment condensing on the inner side of the first lens.

In one example, the condensing member has an inner surface exposed to the air compartment and an outer surface that is exposed to the ambient water. The ambient water directly contacts the outer surface of the condensing member in use.

In one example, the condensing member has a thermal conductivity that is greater than the thermal conductivity of the first lens.

In one example, the condensing member forms a frame that supports the first lens. The frame is interposed between the first lens and the skirt.

In one example, an isolating lens is provided. The isolating lens has an outer surface that faces the inner surface of the first lens. The isolating lens has an inner surface that faces and bounds a portion of the air compartment. The isolating lens and first lens form an isolating air layer therebetween.

In one example, the condensing member is formed from aluminum.

In one example, the condensing member includes an active cooling element. The active cooling element has an inner surface exposed to the air compartment such that the inner surface thermally communicates with the air compartment. The active cooling element including an outer surface that is exposed to the exterior such that, when in the ambient water, the ambient water thermally communicates with the outer surface of the active cooling element. The active cooling element is electrically controlled to actively create a temperature gradient between the inner and outer surfaces of the active cooling element with the outer surface being at a higher temperature than the inner surface.

In one example, the condensing member is in the form of a Peltier element.

In one example, the mask includes a power source for powering the active cooling element. A heating element adjacent the first lens heats the inner surface of the first lens. The heating element is powered by the power source.

In one example, a first temperature sensor is provided that senses the temperature of the air within the air compartment. A second temperature sensor senses the temperature of the ambient water. A controller connects to the first and second temperature sensors and the active cooling element. The controller operably activates and deactivates the active cooling element such that the temperature gradient between the ambient water and the air within the air compartment has a magnitude that is less than a predetermined value. This prevents over cooling of the air compartment that would waste electricity.

In one example, a water contact arrangement within the air compartment senses liquid water within the air compartment. A power source powers the active cooling element. A heating element adjacent the first lens heats the inner surface of the first lens. The heating element is powered by the power source. The controller connects to the water contact arrangement. The controller deactivates the active cooling element when the water contact arrangement senses liquid water within the air compartment.

In an example, a method of preventing condensation on a lens of an underwater mask as outlined above is provided. The method includes wearing the underwater mask within ambient water with the outer side of the first lens in contact with the ambient water. The method includes condensing, with the condensing member, moisture within the air compartment. This occurs prior to condensing the moisture on the inner side of the lens.

In one example, the method includes exposing an inner surface of the condensing member to the air compartment such that there is thermal communication therebetween. The method includes exposing an outer surface of the condensing member to the ambient water such that there is thermal communication therebetween.

In one example, the exposure between the air compartment and the inner surface of the condensing member is direct contact and the exposure between the ambient water and the outer surface of the condensing member is direct contact.

In one example, the condensing member has a thermal conductivity that is greater than the thermal conductivity of the first lens.

In one example, the method includes forming an isolating air layer between an isolating lens and the first lens. The isolating lens has an outer surface that faces the inner surface of the first lens. The isolating lens has an inner surface that faces and bounds a portion of the air compartment.

In one example, the method includes exposing an inner surface of an active cooling element of the condensing member to the air compartment. The method includes exposing an outer surface of the active cooling element to the ambient water. The method includes creating a temperature gradient between the inner and outer surfaces of the active cooling element with the outer surface being at a higher temperature than the inner surface. This may be done by electrically controlling the active cooling element.

In one example, exposing the inner surface of the active cooling element to the air compartment may include direct contact between the inner surface and the air within the air compartment. Exposing the outer surface of the active cooling element to the ambient water may include direct contact therebetween.

In one example, the condensing member is in the form of a Peltier element.

In one example, the method includes heating the inner surface of the first lens with a heating element.

In one example, the method includes powering the active cooling element and the heating element with a same power source. This may, optionally, also include controlling the heating element and active cooling element with a same controller.

In one example, the method includes sensing the temperature of the air within the air compartment. The method includes sensing the temperature of the ambient water. The method includes activating and deactivating the active cooling element such that the temperature gradient between the ambient water and the air within the air compartment has a magnitude that is less than a predetermined value.

In one example, the method includes sensing liquid water within the air compartment. The method includes deactivating the active cooling element when liquid water is sensed within the air compartment.

Other aspects, objectives and advantages of the invention will become more apparent from the following detailed description when taken in conjunction with the accompanying drawings.

BRIEF DESCRIPTION OF THE DRAWINGS

The accompanying drawings incorporated in and forming a part of the specification illustrate several aspects of the present invention and, together with the description, serve to explain the principles of the invention. In the drawings.

While the invention will be described in connection with certain preferred embodiments, there is no intent to limit it to those embodiments. On the contrary, the intent is to cover all alternatives, modifications and equivalents as included within the spirit and scope of the invention as defined by the appended claims.

DETAILED DESCRIPTION OF THE INVENTION

Figure 1:
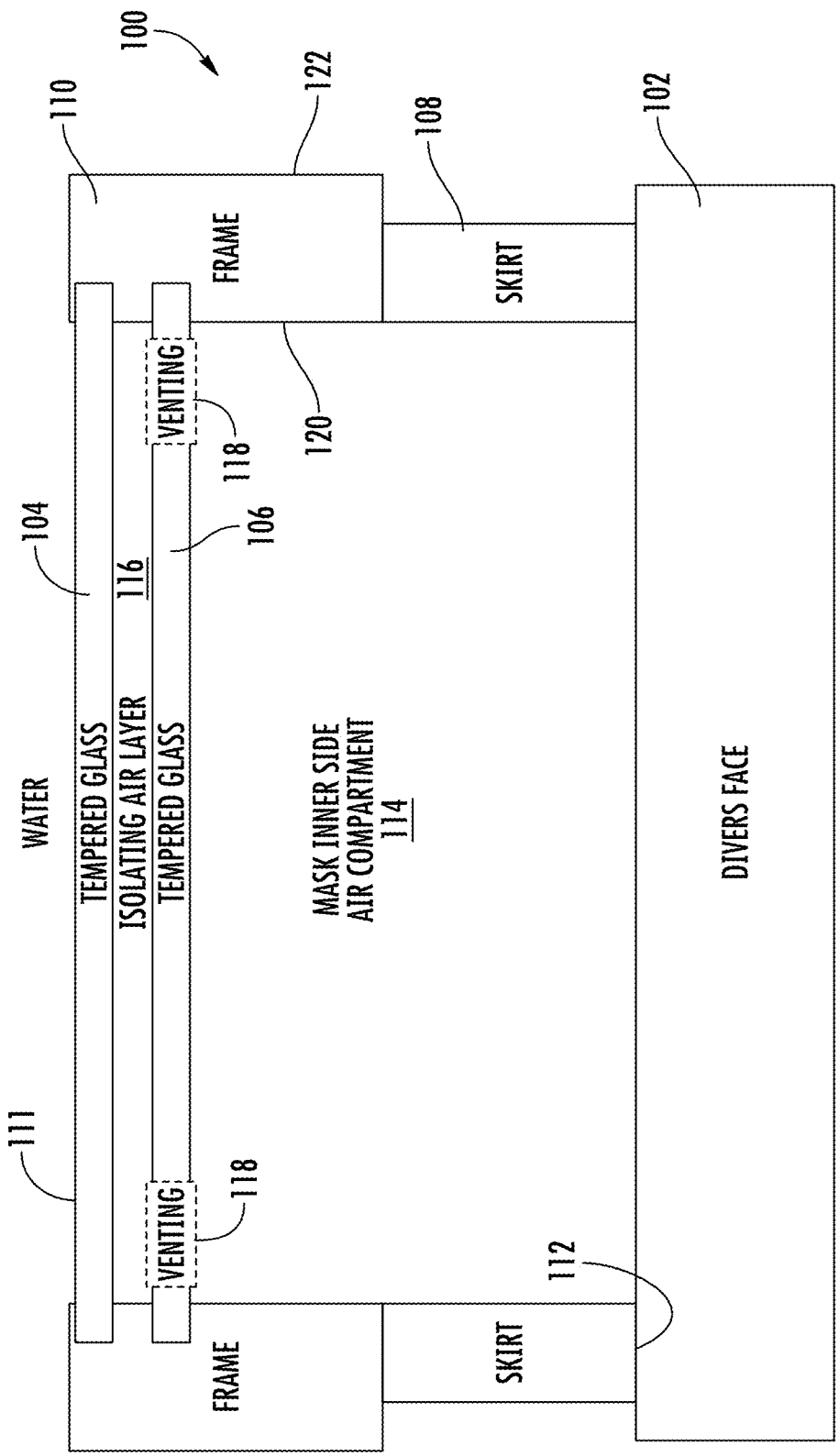
FIG. 1 is a schematic illustration of a first example of an underwater mask according to the present disclosure.

FIG. 1 illustrates a simplified schematic illustration of an example of an underwater mask 100 (also referred to herein as "mask 100") according to the present disclosure. The mask 100 is secured to the face of a diver 102.

The mask 100 includes a front lens 104 (a lens may also be referred to as "glass"), an isolating lens 106, a skirt 108 and a frame 110. In use, skirt 108 is pressed against the face of the diver 102. The skirt 108 will have a sealing interface 112 that is generically shaped to mate with the face of the diver 102. While not shown, the skirt 108 may include or have attached thereto a strap that extends around the diver's head to secure the skirt 108 against the face of the diver 102.

The front lens 104 and isolating lens 106 are mounted to the frame 110. The frame 110 is attached to the skirt 108. The front lens 104 has an outer surface 111 that is directly exposed to the ambient water surrounding the mask 100 when in use.

While the lenses 104, 106 are illustrated as extending across the entire width of the face of the user, in other examples, each of lens 104 and lens 106 could be formed from multiple lens pieces. More particularly, lens 104 could be formed from a pair of lens pieces (one for each eye) and lens 106 could be formed from a pair of lens pieces (one for each eye).

The components of the mask 100 form an air compartment 114.

In use, the air within the air compartment 114 is in direct contact with the face of the diver 102. Typically, the diver's nose and eyes will be in direct communication with the air with in the air compartment 114. As such, the relative humidity and temperature of the air within the air compartment 114 is affected by the diver, such as when the diver equalizes pressure within the air compartment, and is typically raised above the temperature of the ambient water.

In this example, an isolating air layer 116 is formed between the front lens 104 and the isolating lens 106. One or more vents 118 may be provided between isolating air layer 116 and the rest of the air compartment 114 to allow for pressure equalization due to the change in pressure as a diver descends or ascends.

In this example, the frame 110 provides a passive condensing member that inhibits condensation on and fogging of lenses 104, 106 due to temperature gradients when the temperature of the air within the air compartment 114 is greater than the temperature of the ambient water surrounding the mask 100. Instead, the condensing member is configured to condense moisture within the air compartment 114 prior to the moisture within the air compartment.

In this example, the frame 110 has an inner surface 120 in thermal communication with, e.g. exposed to, the air compartment 114 and an outer surface 122 that is in thermal communication with, e.g. exposed to, the ambient water. In preferred examples, the inner surface 120 is in direct contact with the air within the air compartment 114 and the outer surface 122 is in direct contact with the ambient water.

The frame 110 has a thermal conductivity that is greater than the thermal conductivity of the lenses 104, 106. This relationship will cause the frame 110 to dissipate heat energy to the ambient water more quickly than through lenses 104, 106. This causes the inner surface 120 of the frame 110 to be cooler than the surfaces of the lenses 104, 106 that are likewise exposed to the air within the air compartment 114. As such, condensation of moisture within the air within the air compartment 114 will occur on the cooler inner surface 120 of the frame 110 rather than on the surfaces of lenses 104, 106.

In a preferred example, the frame 110 is formed from aluminum.

Notably, the skirt 108, which is typically formed from a rubber, such as silicon, will have a lower thermal conductivity than the material used to form the lenses 104, 106.

In this example, the isolating lens 106 helps insulate the outer lens 104 from the warmer and higher relative humidity air within the air chamber 114. The isolating lens 106 is, however, not required in all examples.

While the frame 110 forms the passive condensing member in this example, in other examples, a passive condensing member could be separate from the frame. The passive condensing member could be a component carried by the skirt and spaced away from the frame 110 and lenses 104, 106. Such a passive condensing member would also have an inner surface exposed to the air compartment 114 and an outer surface exposed to the ambient water.

Figure 2:
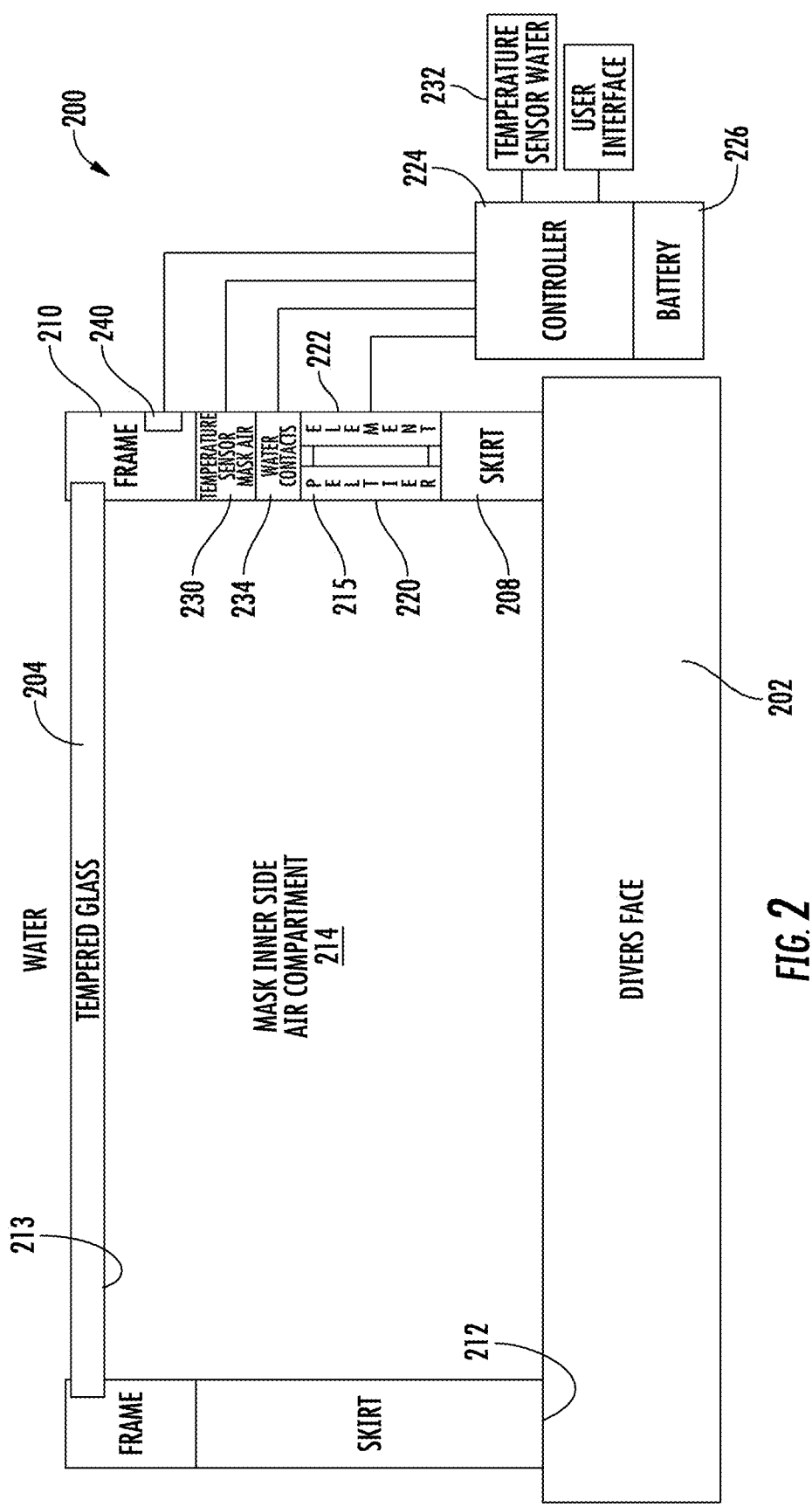
FIG. 2 is a schematic illustration of a second example of an underwater mask according to the present disclosure.

FIG. 2 illustrates a schematic representation of another example of an underwater mask 200 (additionally referred to herein as "mask 200"). The mask 200 is again illustrated pressed against the face of a diver 202. Rather than having a passive condensing member, this example utilizes an active condensing member to inhibit condensation on and fogging of the lens 204.

While only a single lens 204 is illustrated multiple lenses could be incorporated, such as illustrated in FIG. 1.

The lens 204 is illustrated being carried by a frame 210 that is operably coupled to skirt 208. Again, the skirt includes a sealing interface 212 configured to mate with the face of the diver 202.

The lens 204, skirt 208 and frame 210, once again, define an air compartment 214 exposed to the nose, skin and eyes of the diver 202.

In this example, the active condensing member includes a thermoelectric cooling element 215, illustrated in the form of a Peltier element. The thermoelectric cooling element 215 has an inner surface 220 in thermal communication with, e.g. exposed to, the air compartment and an outer surface 222 in thermal communication with, e.g. exposed to, the ambient water. In preferred examples, the inner surface 120 is in direct contact with the air within the air compartment 114 and the outer surface 122 is in direct contact with the ambient water.

The thermoelectric cooling element 215 is operably connected to a controller 224 and battery 226 for selectively powering the thermoelectric cooling element 215. The thermoelectric cooling element 215 is driven such that the inner surface 220 is cooled, and particularly to a temperature that is lower than the inner surface 213 of the lens 204. As such, condensation of moisture within the air within air compartment 214 will condense on inner surface 220 as compared to inner surface 213 of lens 204.

First and second temperature sensors 230, 232 can be provided and can communicate with controller 224. The first temperature sensor 230 senses the temperature of the air within the air compartment 214 while the second temperature sensor 232 sense the temperature of the ambient water.

The controller 224 can regulate thermoelectric cooling element 215 based on the temperature difference between the air within the air compartment 214 and the ambient water to conserve battery 226. More particularly, the controller 224 prevents the air compartment 214 from becoming needlessly too cool relative to the temperature of the lens 204. Here, the lens 204 may be assumed to be or sufficiently close to the temperature of the ambient water. Thus, when the temperature of the air within the air compartment 214 is more than a predetermined amount less than the temperature of the ambient water, the controller 224 can reduce the cooling effect of the thermoelectric cooling element 215. This can be done by reducing power or altogether turning off power to the thermoelectric cooling element 215.

In the illustrated example, optional water contacts 234 are provided that sense liquid water within the air compartment 214. The water contacts 234 are connected to the controller 224. When sufficient liquid water is sensed by the water contacts 234, the controller 224 can be configured to deactivate the thermoelectric cooling element 215.

While the battery 226 and controller 224 are illustrated as a single component, these components could be separate. For instance, the controller 224 could be located proximate the side of a diver's head while the battery 226 could be remote from the controller 224, such as attached to the strap at the back of the diver's head. Alternatively, the controller 224 and battery 226 could be on opposite sides of the divers head so as to balance the weight of the mask 200. Further yet, the battery 226 and/or controller 224 could be integrated into the frame 210.

In one example, the mask 200 may include active heating of the lens 204 and particularly the inner surface 213. This can be done in parallel with the active cooling provided by thermoelectric cooling element 215. For example, the controller 224 could control a heating element 240 that provides heat to the lens 204. Notably, the same battery 226 can be used to power both the heating element 240 as well as the thermoelectric cooling element 215. However, in other embodiments, separate batteries and controllers could be provided.

In one example, the thermoelectric cooling element 215 is carried by the skirt 208 while in other embodiments it may be mounted to frame 210. The same applies to the temperature and water sensors 230, 232, 234.

All references, including publications, patent applications, and patents cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An underwater mask comprising:
   a first lens;
   a skirt for contacting against a wearer and supporting the first lens, the first lens and skirt forming an air compartment, the first lens having an inner side facing the air compartment and an outer side opposite the inner side and facing away from the air compartment; and
   a condensing member carried by the skirt and in communication with the air compartment, the condensing member being configured to condense moisture within air of the air compartment prior to the moisture within the air of the air compartment condensing on the inner side of the first lens; and
   wherein the condensing member includes an active cooling element, the active cooling element has an inner surface exposed to the air compartment such that the inner surface thermally communicates with the air compartment and an outer surface that is exposed to the exterior such that when in the ambient water, the ambient water thermally communicates with the outer surface of the active cooling element, the active cooling element being electrically controlled to actively create a temperature gradient between the inner and outer surfaces of the active cooling element with the outer surface being at a higher temperature than the inner surface.

2. The underwater mask of claim 1, wherein the condensing member is in the form of a Peltier element.

3. The underwater mask of claim 1, further comprising:
   a power source for powering the active cooling element;
   a heating element adjacent the first lens for heating the inner surface of the first lens, the heating element being powered by the power source.

4. The underwater mask of claim 1, further comprising:
   a first temperature sensor sensing the temperature of the air within the air compartment;
   a second temperature sensor sensing the temperature of the ambient water;
   a controller connected to the first and second temperature sensors and the active cooling element, the controller operably activating and deactivating the active cooling element such that the temperature gradient between the ambient water and the air within the air compartment has a magnitude that is less than a predetermined value.

5. The underwater mask of claim 4, further comprising:
   a water contact arrangement within the air compartment configured to sense liquid water within the air compartment; and
   a power source for powering the active cooling element;
   a heating element adjacent the first lens for heating the inner surface of the first lens, the heating element being powered by the power source;
   the controller connected to the water contact arrangement, the controller configured to deactivate the active cooling element when the water contact arrangement senses liquid water within the air compartment.

6. The underwater mask of claim 1, further comprising:
   a water contact arrangement within the air compartment configured to sense liquid water within the air compartment; and a controller connected to the active cooling element and the water contact arrangement, the controller configured to deactivate the active cooling element when the water contact arrangement senses liquid water within the air compartment.

7. The underwater mask of claim 1, wherein the inner surface of the active cooling element directly contacts the air within the air compartment and the outer surface directly contacts the ambient water when in use.

8. A method of preventing condensation on a lens of an underwater mask of claim 1, comprising:
wearing the underwater mask within ambient water with the outer side of the first lens in contact with the ambient water;
condensing, with the condensing member, moisture within the air compartment;
exposing an inner surface of an active cooling element of the condensing member to the air compartment;
exposing an outer surface of the active cooling element to the ambient water such that the ambient water directly contacts the outer surface of the active cooling element;
creating a temperature gradient between the inner and outer surfaces of the active cooling element with the outer surface being at a higher temperature than the inner surface, by electrically controlling the active cooling element.

9. The method of claim 8, wherein the condensing member is in the form of a Peltier element.

10. The method of claim 8, further comprising:
heating the inner surface of the first lens with a heating element.

11. The method of claim 10, further comprising powering the active cooling element and the heating element with a same power source.

12. The method of claim 8, further comprising:
sensing the temperature of the air within the air compartment;
sensing the temperature of the ambient water; and
activating and deactivating the active cooling element such that the temperature gradient between the ambient water and the air within the air compartment has a magnitude that is less than a predetermined value.

13. The method of claim 8, further comprising:
sensing liquid water within the air compartment; and
deactivating the active cooling element when liquid water is sensed within the air compartment.

* * * * *